United States Patent [19]

Gibson

[11] Patent Number: 4,983,580
[45] Date of Patent: Jan. 8, 1991

[54] METHODS AND MATERIALS FOR USE IN CORNEAL WOUND HEALING

[75] Inventor: David R. Gibson, Irvine, Calif.

[73] Assignee: Allergan, Inc., Irvine, Calif.

[21] Appl. No.: 467,116

[22] Filed: Mar. 7, 1990

Related U.S. Application Data

[62] Division of Ser. No. 848,279, Apr. 4, 1986, abandoned.

[51] Int. Cl.$^5$ .................... A01N 37/18; A01N 43/04; A61K 37/00; A61K 37/715
[52] U.S. Cl. .......................................... 514/2; 514/21; 514/54; 514/56; 514/62; 514/801; 514/953
[58] Field of Search .................. 514/2, 21, 54, 56, 62, 514/773, 777, 801, 953, 954; 530/395, 396, 356, 382

[56] References Cited

U.S. PATENT DOCUMENTS 4,458,678  7/1984  Yannas et al. ................ 128/155
4,486,416  12/1984  Soll et al. ........................ 514/54

FOREIGN PATENT DOCUMENTS 0190018  8/1986  European Pat. Off. .

OTHER PUBLICATIONS

Kawaba et al., "Effect of Human EGF and Plasma Fibronectin on Corneal Epithelial Regeneration", Nippon Ganka Gakkai Zasshi, 88(9) 1237-44, 1984.
Nishida et al., *Ophthalmology*, 92(2):213-216, Feb. 1985.
Nishida et al., *Arch Ophthalmol*, 101:1046-1048, Jul. 1983.

*Primary Examiner*—Nathan M. Nutter
*Attorney, Agent, or Firm*—Bernard, Rothwell & Brown

[57] ABSTRACT

Improvement in healing of wounds of the corneal stroma is obtained by placing into the wounds a corneal mortar composition comprising an extracellular matrix material and an ophthalmologically compatible carrier material, the composition having a sufficiently high viscosity to retain it within the wound under wound-healing conditions.

15 Claims, 3 Drawing Sheets

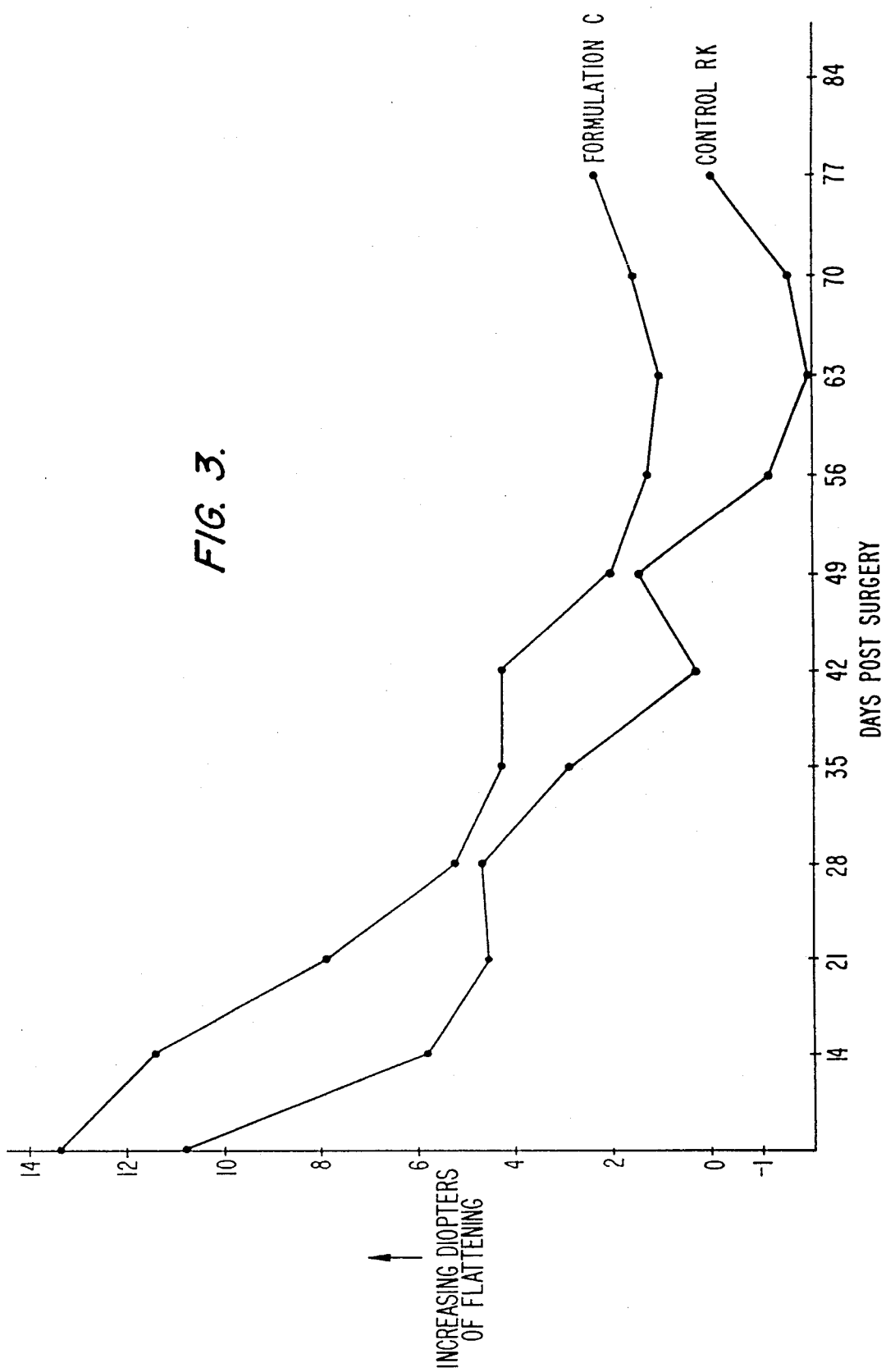

METHODS AND MATERIALS FOR USE IN CORNEAL WOUND HEALING

This is a division of U.S. application Ser. No. 848,279, filed Apr. 4, 1986 now abandoned.

BACKGROUND OF THE INVENTION

This invention relates to methods and materials which have beneficial effects in promoting the healing of wounds of the eye. The methods and materials of the invention are particularly useful in promoting the healing of corneal incisions made during keratorefractive surgical procedures such as radial keratotomy. In keratorefractive surgical procedures, the methods and materials of the invention can improve the degree of refractive correction and/or provide for greater control and predictability of the results, as well as reduce scarring and improve cosmetic appearance.

Ophthalmologists have long been concerned with the treatment of vision problems caused by defects in the geometry of the eye. The most common of these problems include myopia (nearsightedness) caused by excessive corneal curvature and astigmatism, a refractive problem caused by corneal asymmetry. In recent years, a great deal of interest has developed in the use of surgical procedures—known generally as keratorefractive surgeries—which correct these conditions by surgically altering corneal geometry. If successful, such techniques offer readily apparent advantages over the conventional methods of vision correction, i.e., the use of corrective lenses such as eyeglasses or contact lenses. Corrective lenses are often inconvenient or uncomfortable to wear and are subject to loss or breakage. Contact lenses present a risk of corneal abrasion and/or infection. These problems could be avoided if reliable keratorefractive surgical procedures could be developed that produce predictable, permanent vision correction.

Radial keratotomy is a keratorefractive surgical procedure which is employed to correct myopia caused by excessive corneal curvature. In this technique, a series of incisions is made in the cornea, usually penetrating about 90 to 95% of the thickness of the cornea. The incisions, which are usually about 3 mm in length, extend along lines which radiate outwardly from the corneal center. The number of incisions may vary from as few as four to as many as 16, with 8 to 12 being commonly employed. The incisions allow the cornea to relax and to flatten out somewhat, thereby reducing or eliminating nearsightedness. Similar procedures, in which corneal incisions in directions other than radial directions, have been employed to correct some astigmatisms.

While radial keratotomy and related keratorefractive surgeries have become fairly commonplace, the results achieved using presently available techniques are not highly predictable or controllable in any given patient. In particular, the degree of correction, measured in diopters, is not well controlled and may be more or less than is needed by the particular individual, so that the operation may have to be repeated or corrective lenses may still be needed. Furthermore, the healing process usually takes from 12 to 24 months, during which time some patients experience instability in visual acuity; that is, the cornea begins to reacquire some of the curvature lost as a result of the operation. Maximum flattening of the cornea usually occurs about 2 days after surgery, with a gradual increase in curvature occurring thereafter until the incisions have healed.

Some keratotamy patients have also encountered post-operative vision problems related to scarring. In some instances, scars at the healed incision sites cause light to be reflected within the eye, resulting in a perceived glare, particularly at night. Fluctuations in visual acuity throughout the day may also result.

The aforementioned problems encountered in keratorefractive surgery are related to the manner in which the corneal incisions heal. Yet, no efforts appear to have been made to improve the results obtained in keratorefractive surgery by significantly altering the course of healing of the surgical incisions.

A number of substances have been discussed in the literature in connection with corneal wound healing. Fibronectin, a plasma and extracellular matrix glycoprotein, has been applied as a topical wound-healing agent in the treatment of wounds or defects of the epithelial layer of the cornea (see Phan, T.M. et al., *ARVO 1985 Supplement to Investigative Ophthalmology & Visual Science*, Vol. 26, No. 3, p. 92 (1985); Nishida et al., *Arch. Ophthalmol.*, 101:1046-1048 (1983); Nishida et al., *Ophthalmology*, 92, 2, 213-216 (1985)). The appearance of fibronectin at the edges of stromal wounds in rabbit eyes was reported by Suda and coworkers. (*Current Eye Research*, 1, 9, 553-556 (1982)). Dweck and coworkers have reported that type IIIc collagen and fibronectin are deposited at the site of stromal wounds in rabbits T.M. et al., *ARVO 1985 Supplement to Investigative Ophthalmology & Visual Science*, Vol. 26, No. 3, p. 92 (1985).

The mechanisms of healing of deep stromal wounds, such as the incisions made during keratorefractive surgery, are considerably more complex than those involved in epithelial wound healing and are generally not as well understood. The incisions which are made during a keratotamy exhibit V-shaped cross-sectional configurations. They penetrate through the epithelium (outer corneal layer), the basement membrane, Bowman's membrane and most of the thickness of the stroma (the thick structural layer of the cornea), leaving only Descemet's membrane and the endothelium completely intact.

SUMMARY OF THE INVENTION

This invention provides methods and compositions for enhancing the healing of wounds of the corneal stroma. The methods and compositions of the invention can substantially enhance the results obtainable in keratorefractive surgery by altering the course of healing of surgical incisions of the corneal stroma. Using the methods and compositions of the invention, substantial improvements can be obtained in the degree of refractive correction obtainable in keratorefractive surgery. Moreover, the degree of refractive correction obtained in a given patient is much more controllable and predictable than it is using prior art procedures. The methods and compositions of the invention can also promote more controlled healing of the surgical incisions, reduce glare caused by scarring and improve cosmetic results.

In accordance with the method of the invention, a corneal mortar composition is placed into a wound which extends into the stromal tissue in order to enhance wound healing. The corneal mortar composition of the invention serves the function of providing a matrix for the migration of keratocytes and for the deposition of wound healing substances in the wound site.

In the case of keratorefractive incisions, the corneal mortar composition serves to help maintain the original spatial relationship between the walls of the incision while wound healing occurs. That is, the corneal mortar which is deposited in the incisions prevents the incision walls from drawing back together during healing, thereby partially reversing the effect of the procedure. Consequently, the cornea tends to retain the geometric alterations imparted by the incisions and visual acuity tends to remain stable through the course of healing.

The corneal mortar composition which is employed in the practice of the invention, comprises an extracellular matrix (ECM) material, such as fibronectin, and an ophthalmologically compatible carrier material having a sufficiently high viscosity to cause the ECM material to be retained within the wound during healing. In a preferred embodiment of the invention, the corneal mortar composition contains two ECM materials, fibronectin and chondroitin sulfate, and a growth factor such as epidermal growth factor.

BRIEF DESCRIPTION OF THE DRAWINGS

FIG. 3 is a graph presenting plots of corneal flattening versus post-surgical time for radial keratotamies in primates. One plot represents corneal flattening in primates in which corneal mortar composition of the invention was placed in the surgical incisions. The other plot represents controls in which only the saline carrier vehicle was placed in the incisions.

DETAILED DESCRIPTION OF THE INVENTION

I. The Corneal Mortar Composition

Figure 1A:
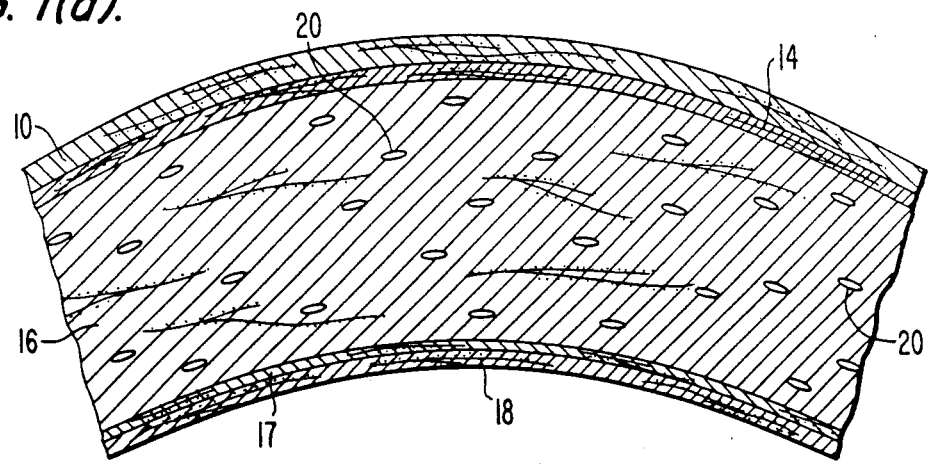
FIG. 1(a) illustrates a cross-section of a portion of an intact cornea.

The corneal mortar composition of the invention comprises at least one ECM material and an ophthalmologically compatible carrier material, the composition having a sufficiently high viscosity to retain the ECM material within the wound during healing ECMs are materials which can be found in extracellular matrix structures laid down by cultured cells. (Hsieh, P. and Baum, J., *Invest. Ophth. & Vis. Sci.*, 26:457-463 (1985)). ECM materials include extracellular matrix proteins and extracellular ground substances. The former are generally high molecular weight (>150,000 daltons) fibrinous glycoproteins, which include fibronectin, collagens, vitronectin, elastin, laminin, actin and fibrinogen. The latter are polysaccharides, glycosylaminoglycans, which include chondroitin sulfate, heparin, keratin sulfate and hyaluronic acid or its sodium salt.

A preferred ECM material for use in the corneal mortar composition is fibronectin. Preferably, fibronectin is present in the corneal mortar composition even if other ECM materials are also employed Fibronectin can be present in the corneal mortar composition in amounts from about 0.5% to about 90%, preferably from about 2% to about 40% by weight of the composition. Fibronectin is a glycoprotein (4-5% carbohydrate) having a molecular weight of about 220,000 daltons, which exists in the form of a 440,000-dalton dimer. Fibronectin exists in a plasma associated form and a cell associated form. It can conveniently be isolated from plasma by the procedure described by Nishida et al., *Jap. J. Ophth.*, Vol. 26, pp. 416-24 (1985). Fibronectin is also known by various other names, including cold-insoluble globulin, surface fibroblast antigen, cell surface protein, band 1, L1 band, band I, zeta-protein, major fibroblast glycoprotein, galactoprotein A, large external transformation sensitive protein (LETS), micro-fibrillar protein, cell attachment protein, cell adhesion factor, anti-gelatin factor, cell spreading factor and opsonic factor. For a review of the structure and activities of fibronectin, see Pearlstein, et al , *Mol & Cell. Biochem.*, 29:103-125 (1980). Additionally, ECM proteins having a high degree of amino acid sequence homology with fibronectin, such as vitronectin (Suzuki, S., *J. Biol. Chem.*, 259:15307-15314 (1984) can be used in the preferred embodiment.

In a preferred embodiment of the invention, the corneal mortar composition contains both fibronectin and chondroitin sulfate. Chondroitin sulfate is a glycosylaminoglycan found in the ECM's of animal connective tissues. It is a polymer formed of repeating disaccharide units. Each repeating disaccharide unit contains one sulfate group. Chondroitin sulfate has three isomers (chondroitin sulfate A, chondroitin sulfate B and chondroitin sulfate C), which differ in the position of the sulfate group in the disaccharide unit. All three isomers are useful in the corneal mortar compositions of the invention. Chondroitin sulfate can be obtained from commercial sources. Chondroitin sulfate can be present in the corneal mortar composition in amounts from about 0.5% to about 75% by weight of the composition.

The corneal mortar composition can also contain collagen, an ECM material which is present in normal stromal tissue. Preferably, the amount of collagen, if present, does not exceed about 50 weight percent of the composition. While any type of collagen is suitable for use in the corneal mortar composition, Type I bovine collagen is preferred.

Laminin, which is another ECM material present in normal stromal tissue, can also be present in the corneal mortar composition in amounts up to about 75% by weight of the composition.

Fibrinogen, which is also an ECM material, can be present in the corneal mortar composition in amounts up to about 40% by weight thereof.

Advantageously, the corneal mortar composition of the invention also contains a growth factor such as epidermal growth factor. Growth factors are mitogenic proteins or polypeptides which promote cell proliferation. A number of growth factors are known. These include epidermal growth factor (EGF), transforming growth factors (TGF's) and nerve growth factor (NGF). Insulin, a polypeptide hormone, has mitogenic activity and can be used in conjunction with prostaglandin $F_{2\alpha}$, a non-peptide which has been shown to increase greatly the mitogenic activity of insulin (see Jimenez de Asua, L. et al., *Cold Spring Harbor Conf. Cell Proliferation*, Vol. 6, Sato, ed., Cold Spring Harbor Labs., New York [1979], at 403–424). Similar activation of insulin has been reported with fibroblast growth factor by Rudland, P.S. et al., *Proc. Natl. Acad. Sci., U.S.A.*, 76:1279–1293 (1974). Positive effects on cell growth have been demonstrated for platelet-derived growth factor or fibroblast-derived growth factor in combination with members of the insulin family such as somatomedins A and C (Stiles, C.D. et al., *Proc. Natl. Acad. Sci., U.S.A.*, 76:1279–1283 [1979]). Additionally, many new peptide growth factors have been isolated and characterized recently as indicated in *Tissue Growth Factors*, R. Baserga, ed., Springer-Verlag pub., New York (1981). The present invention contemplates the use of any of the known growth factors, alone or in combination, in conjunction with ECM materials in the corneal mortar compositions of the invention.

A preferred growth factor for use in the corneal mortar compositions of the invention is epidermal growth factor. EGF can be obtained from human tissues by the procedure described by Urdea et al., *PNAS (USA)*, Vol. 80, p. 7461.

If present in the corneal mortar composition of the invention, the growth factor is employed in an amount which is effective to promote stromal cell growth at the wound site. Generally, the growth factor can be present in the corneal mortar composition at a concentration from about 0.01 μg/ml to about 100 μg/ml, preferably from about 0.1 μg/ml to about 10 μg/ml, although there is no strict upper limit to the concentration of growth factor.

There is also present in the corneal mortar composition of the invention an ophthalmologically compatible carrier material. The carrier material is selected to act as a viscosity-adjusting agent, normally a diluent, to produce the desired viscosity in the corneal mortar composition. The carrier is normally a solution which is buffered to physiological pH, i.e., from about 6.5 to about 7.8. Phosphate buffered saline solution (PBS) is a preferred carrier material. Other suitable carrier materials include distilled water, ophthalmic saline solutions and other ophthalmic buffers, artificial tear materials, and viscoelastic agents such as sodium hyaluronate.

The corneal mortar composition of the invention has a viscosity sufficiently high that the ECM material is retained within the wound during wound healing. That is, at least a sufficient amount of ECM material is retained in the wound to establish a matrix for healing. Since ECM materials bind to the stromal surfaces and establish a matrix rather quickly, it is sufficient if the composition has the consistency of a viscous fluid, so that it is not washed out of the wound by lacrimal secretions. Advantageously, the composition has a thick, pastelike viscosity. Since fibronectin and chondroitin sulfate are viscous materials, they are capable of imparting the desired viscosity to the corneal mortar compositions even at low concentrations. Fibronectin by itself begins to impart the desired viscosity when dissolved in saline solutions at concentrations of about 2% or higher. Chondroitin sulfate by itself begins to impart the desired viscosity when dissolved in saline at levels as low as about 1%. While there is no strict upper limit on the viscosity of the composition, it should not be so viscous that it cannot be inserted into the wound by the physician.

Other ophthalmologically compatible substances which optionally can be present in the corneal mortar composition include substances which are known to promote wound healing or combat infection or inflammation. For example, antibiotics can be present in the compositions in known effective amounts.

In one embodiment of the invention, the corneal mortar composition comprises fibronectin and an ophthalmologically compatible carrier material, the composition having a viscosity sufficiently high to retain the composition in the wound. The following formulation is exemplary of this embodiment:

| Ingredient | Amount* |
|---|---|
| Fibronectin | 2.0–40% |
| PBS | 60–98% |

*Percentages based on total composition weight

In another embodiment, the corneal mortar composition comprises fibronectin, chondroitin sulfate and an ophthalmologically compatible carrier material, the composition having a viscosity sufficiently high to retain the composition in the wound. The following formulation is exemplary of this embodiment:

| Ingredient | Amount |
|---|---|
| Fibronectin | 0.5–40% |
| Chondroitin sulfate | 0.5–75% |
| PBS | 25–99% |

In another embodiment of the invention, the corneal mortar composition comprises fibronectin, a growth factor and an ophthalmologically compatible carrier material, the composition having a sufficiently high viscosity to retain the composition in the wound. The following formulation is exemplary of this embodiment:

| Ingredient | Amount |
|---|---|
| Fibronectin | 0.5–40% |
| PBS | 60–99.5% |
| EGF | 0.01–100 μg/ml |

In yet another embodiment, the corneal mortar composition comprises fibronectin, chondroitin sulfate, collagen and an ophthalmologically compatible carrier material, the composition having a sufficiently high viscosity to retain the composition in the wound. The following formulation is exemplary of this embodiment:

| Ingredient | Amount |
|---|---|
| Fibronectin | 0.5–40% |
| Chondroitin sulfate | 0.5–75% |
| Collagen | 0.5–50% |
| PBS | 25–98.5% |

In a preferred embodiment, the corneal mortar composition comprises fibronectin, chondroitin sulfate, a growth factor and an ophthalmologically acceptable carrier material, the composition having a sufficiently high viscosity to retain the composition in the wound. The following formulation is exemplary of this embodiment:

| Ingredient | Amount |
|---|---|
| Fibronectin | 0.5–40% |
| Chondroitin sulfate | 0.5–75% |

| Ingredient | Amount |
| --- | --- |
| PBS | 25–99% |
| EGF | 0.01–100 µg/ml |

Compositions of the invention which contained chondroitin sulfate or fibronectin as the sole ECM material did not result in improved flattening following radial keratotamy in cat studies. Histological studies, however, showed that the use of chondroitin sulfate or fibronectin as the sole ECM material resulted in reduced scarring as a result of improved organizational integrity of the healed tissue.

The use of epidermal growth factor in combination with chondroitin sulfate and the use of epidermal growth factor in combination with fibronectin each provided a synergistic effect in the enhancement of corneal flattening. Although EGF is known to promote wound healing generally, the use of EGF alone as a wound healing agent following radial keratotamy tends to reverse the beneficial effect of the surgery on visual acuity even though it speeds healing of the incisions. Furthermore, chondroitin sulfate or fibronectin as a sole ECM material each resulted in decreased flattening as compared with controls in cat studies. However, when EGF was used in conjunction with fibronectin or chondroitin sulfate, improved corneal flattening was obtained.

II. The Method of the Invention

The methods of the invention will be described below with specific reference to the use of the corneal mortar composition to treat keratorefractive incisions, thereby enhancing the improvement in visual acuity and/or reducing scarring. It is to be understood, however, that the corneal mortar compositions can also be used in a similar manner to treat corneal wounds of a non-surgical nature which extend into the stromal tissue and that the corneal mortar composition will have beneficial effects in the healing of such wounds.

The use of the corneal mortar composition of the invention in keratorefractive surgery can be understood with reference to the figures.

FIG. 1(a) illustrates a cross-section of a portion of an intact cornea The outer layer, i.e., the layer on the convex surface of the cornea, is the epithelium 10, which is normally about 5 cells thick. Under the epithelium 10 is the Bowman's membrane 14 (present only in primates). The Bowman's membrane 14 separates the epithelium 10 from the stroma 16, the relatively thick structural layer of the cornea. The stroma 16 is comprised of macromolecules, including collagen, chondroitin sulfate and keratin sulfate, as well as cells. Descemet's membrane 17 separates the stroma 16 from the endothelium 18. The endothelium 18 is a membrane of single-cell thickness which separates the stroma 16 from the aqueous humor (not shown) and serves to regulate fluid transport to and from the stroma 16. Keratocytes 20 are distributed throughout the stroma 16.

Figure 1B:
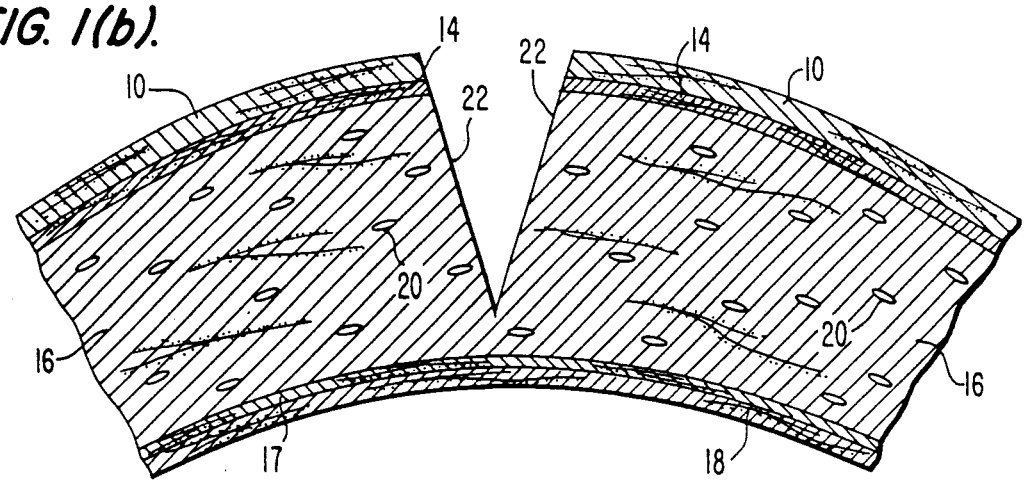
FIG. 1(b) illustrates a cross-section of a portion of a cornea immediately after keratorefractive surgery.
Figure 1C:
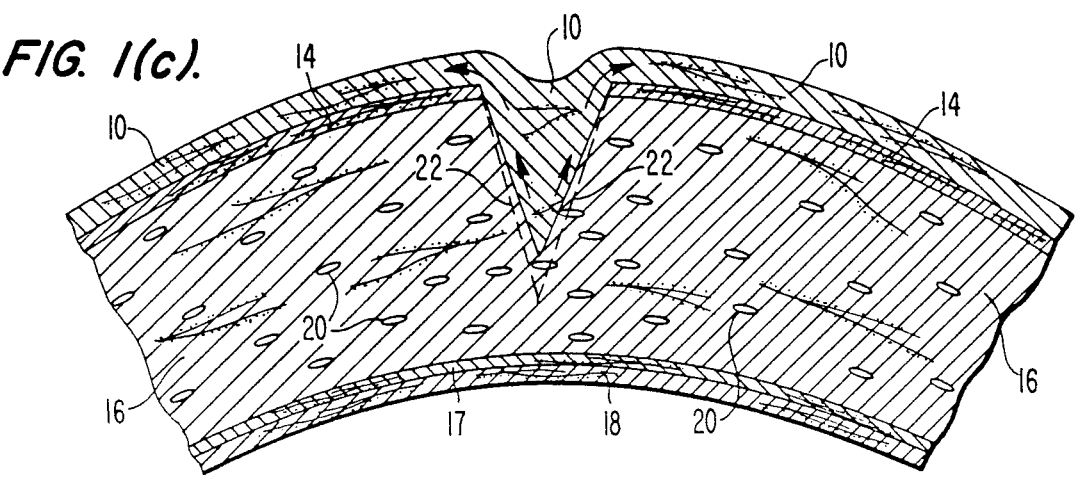
FIG. 1(c) illustrates a cross-section of a portion of a cornea approximately 3-5 days after keratorefractive surgery in which the method and composition of the invention were not employed.
Figure 1D:
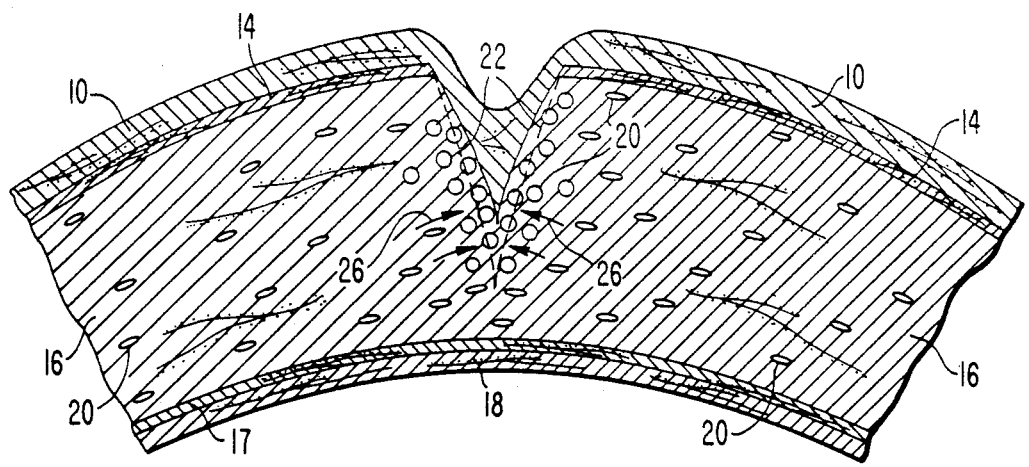
FIG. 1(d) illustrates a cross-section of a portion of a cornea approximately 28 days after keratorefractive surgery in which the method and composition of the invention were not employed.

FIG. 1(b) illustrates a cross-section of a portion of a cornea immediately after keratorefractive surgery in which an incision having a V-shaped cross section has been made into the stroma 16. The incision has allowed the cornea to relax and flatten out somewhat, thereby changing the refraction of the cornea to reduce or eliminate myopia. FIG. 1(c) illustrates the same cross-sectional portion of the cornea as it would appear about 3–5 days after surgery without the use of the corneal mortar composition of the invention. The position of the stromal tissue surfaces forming the original incision walls 22 is indicated in FIGS. 1(c) and 1(d) by a dashed line. The healing process can only occur along the surfaces of the walls 22 of the incision and only after those surfaces have been epithelialized; that is, epithelial cells must grow down from the epithelium 10 to cover the entire surface of the walls 22 of the incision. In effect, the epithelium 10 must extend itself down to the bottom of the "V" of the incision in order for healing to take place. As shown in FIG. 1(c), the closing of the incision wound begins at the bottom of the "V" and works its way upward. As the wound heals in from the bottom of the "V", the epithelial cells which have extended into the wound must be pushed out of the wound in a direction indicated by arrows in FIG. 1(c). The ability to displace the epithelial cells from the wound site may be a rate-limiting factor in wound healing.

In the normal course of healing of the incision, i.e., without the corneal mortar composition, the walls 22 of the incision tend to be drawn together, starting from the bottom of the "V", in a zipperlike fashion. This can be seen more clearly in FIG. 1(d), which illustrates the typical condition of the incision wound about 28 days after surgery. As the wound has healed, from the bottom upward, the stromal tissue surfaces which formed the original walls 22 of the incision have been drawn somewhat closer together, i.e., in the direction indicated by the arrows 26 in FIG. 1(d).

In accordance with the method of the invention, the corneal mortar composition is inserted into the incisions during keratorefractive surgery. The corneal mortar composition can be inserted into the wound as a coating on the walls 22 of the incisions. Preferably, however, the amount of corneal mortar composition which is placed in the incision is sufficient not only to coat the walls 22 of the incision but also to fill in at least a portion of the space between the walls 22 of the incision.

Figure 2:
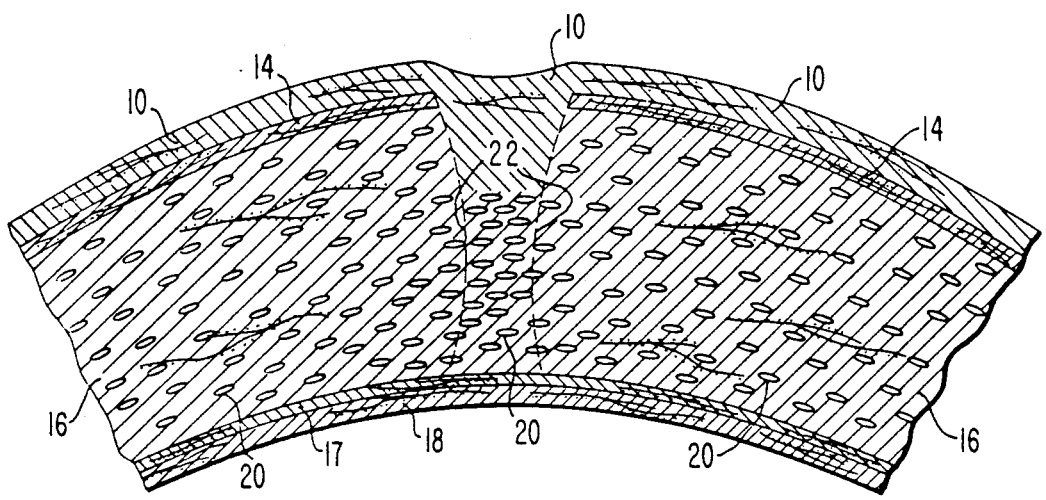
FIG. 2 illustrates a cross-section of a portion of a cornea approximately 28 days after keratorefractive surgery in which the corneal mortar composition of the invention has been inserted into the incisions.

FIG. 2 illustrates a cross-section of a portion of a cornea approximately 28 days after keratorefractive surgery in which the corneal mortar composition of the invention has been deposited into the incision wound. It is preferred that at least about 1% of the space between the walls 22 of the incision be filled. It is particularly desirable that the posterior portion of the incision, i.e., the portion of the incision at the bottom of the "V", be completely filled.

The corneal mortar composition provides a matrix for the deposition of wound-healing substances and for cell migration and growth. Thus, the wound-healing process is no longer constrained to take place at the surfaces of the incision, but rather, it can take place concurrently throughout the volume of space occupied by the corneal mortar composition. Placing the corneal mortar composition into the incision induces keratocytes 20 to migrate into the space between the walls 22 of the incision where they grow and deposit wound-healing substances such as collagen. Importantly, from the point of view of enhancing the results obtained in keratorefractive surgery, the corneal mortar composition in the incision maintains space between the walls 22 of the incision throughout the healing process, i.e., it prevents the stromal tissue surfaces which formed the original incision walls 22 from being drawn together in the manner illustrated in FIGS. 1(c) and 1(d). This is illustrated in FIG. 2 by the position of the dashed lines representing the original walls 22, which have not drawn together following surgery, and have moved apart somewhat at the base of the incision. Consequently, the effect of the surgery in adjusting the curvature of the cornea is not reversed by the healing process.

A further advantage of using the corneal mortar composition of the invention relates to the organizational integrity of the healed tissue. Keratocytes, which are somewhat disc-shaped, are oriented in the plane of the "grain" in normal stromal tissue. Consequently, when viewed microscopically in a cross-section of normal cornea, they are seen on edge and appear relatively narrow as seen in FIG. 1(a). When wound healing proceeds without the benefit of the corneal mortar composition, as seen in FIG. 1(d), keratocytes 20 are distributed within the healed area in a random orientation so that some of them appear round on microscopic inspection. This random orientation results in collagen being laid down from the edges of the keratocytes 20 in a swirling manner, rather than aligned with the grain of the stromal tissue. On the other hand, when the corneal mortar composition of the invention is deposited in the wound, it provides a matrix which properly orients the keratocytes 20, as shown in FIG. 2, so that collagen is laid down with the grain of the stromal tissue. The lack of orientation of keratocytes 20 in control animals was associated with increased scarring and cosmetically poor healing.

The use of the corneal mortar composition of the invention may also speed the healing process. As previously mentioned, use of the composition frees the healing process from the geometric constraints of the wound surfaces. Moreover, the composition appears to promote epithelialization of the incision surfaces which is necessary for healing to occur.

The corneal mortar composition can be placed into the surgical incision by the surgeon using any convenient means, such as by injection through a large-bore needle or by the use of any suitable trowel-like tool. The particular method which is best will depend largely on the viscosity of the corneal mortar composition.

If desired, a soft contact lens which is permeable to gas and moisture may be placed over the cornea postoperatively in order to allow moisture transmission while insuring that the corneal mortar composition remains in the incision. Alternatively, a hard contact lens, which forces the cornea to conform to the contact lens geometry, may be placed over the cornea in order to fix the desired shape of the cornea during the healing process.

Using the method of the invention, a substantially increased degree of refractive correction can be obtained in many instances. For example, radial keratotamies were performed in rabbits in which one eye was a control which received no corneal mortar while the incisions in the other eye were packed with a corneal mortar composition containing 50 mg fibronectin, 2.6 gm, chondroitin sulfate and 13–15 mg collagen in phosphate buffered saline. After 7 days of healing, corneascopic examination revealed that the corneas which received the corneal mortar composition exhibited from 12 to 15 diopters of flattening, compared with only 3 to 4 diopters for the control eyes. Moreover, the degree of corneal flattening gradually lessened in the control eyes after the second day of healing, whereas it underwent a slight increase in the eyes which received the corneal mortar composition. Because of the significant increase in the degree of flattening obtainable with the method of the invention, it may be possible in many instances to reduce the number of incisions required to obtain the desired degree of refractive correction and/or to reduce the depth of the incisions. Reducing the depth of the incisions in turn reduces the danger of corneal perforation during surgery.

The following examples are intended to illustrate the practice of the invention further and are not to be construed as limiting the scope of the invention in any way.

EXAMPLE I

Radial keratotamies were performed on a number of cats. Preoperative treatment consisted of weight measurement, slit lamp examination, specular microscopy and corneascope examination. A tattoo was placed at the center of the cornea.

To perform radial keratotamy, each animal was sedated with an intramuscular injection of ketaminexylazine and each eye was then treated with a topical anesthetic. The eye was irrigated with preservativefree ophthalmic saline. For radial keratotamy, the optical zone was set by a 3-mm trephine at the central corneal tatoo. Using a ruby knife, an incision was made to 90% of the depth of the lowest corneal thickness based on pachometry readings taken prior to cutting. Radial keratotamy incisions were made at 12, 3, 6 and 9 o'clock and extended from the end of the 3-mm zone to the limbus.

Each cut was irrigated using a 27-g irrigation cannula with syringe containing preservative-free ophthalmic saline solution. The incision was dried with a cotton-tipped applicator or gauze. Following radial keratotamy, one of various compositions was inserted into the incisions in each of the eyes, except for the control eyes, which received no treatment. In Table 1, which indicates the various compositions which were employed, the abbreviation "Fn" indicates fibronectin; "CS" indicates chondroitin sulfate A; "EGF" indicates epidermal growth factor; and "PBS" indicates phosphate buffered saline.

TABLE 1

| | Treatment Matrix for Cats | |
|---|---|---|
| No. of Cats | Left Eye (OS) | Right Eye (OD) |
| 4 Cats | Control | Fn |
| | RK | 0.25 mg Fn + 1.5 ml Saline |
| | No Treatment | liquid |
| 4 Cats | Fn + CS | Fn + CS + EGF |
| | 25 mg Fn | ⅓ g. CS |
| | ⅓ gm CS | 25 mg Fn |
| | 0.7 ml saline | 15 mg EGF |
| | Very thick | 0.7 ml saline |
| | | Very thick |
| 4 Cats | CS + EGF | EGF |
| | 15 µg EGF | 15 µg EGF |
| | 1.3 gm CS | 1.5 ml saline |
| | 1.1–1.2 ml saline | liquid |
| | thick paste | |
| 4 Cats, one eye only | CS | |
| | 1.3 gm CS | |
| | 1.3 ml saline | |
| | thick paste | |
| 3 Cats, one eye only | Control | |
| | RK | |

After 56 days, the amount of corneal flattening in each eye was determined using a corneascope. The average amount of flattening, measured in diopters, was determined for the treatment and control groups. The results are presented in Table 2.

TABLE 2

Day 56 Corneal Flattening*

| Treatment Group | Diopters of Flattening |
| --- | --- |
| Epidermal Growth Factor (EGF) | 1.5 |
| Fibronectin | 1.5 |
| Chonodroitin Sulfate, Fibronectin and EGF | 1.9 |
| Chondroitin Sulfate | 2.7 |
| Control | 3.1 |
| Chondroitin Sulfate & EGF | 3.8 |
| Chondroitin Sulfate & Fibronectin | 3.8 |

*Average value all eyes in each respective group

Histological studies of cat tissue samples by light microscopy and electron microscopy indicated that the organizational integrity of the incisions was improved in all the treatment groups versus the controls. Treated animals, to varying degrees, displayed an intrastromal keratocyte population that was laid down flatly between the stromal bands, in the manner illustrated in FIG. 2. By comparison, many of the keratocytes in the control animals exhibited a round appearance and were less organized. The flat distribution in the treatment animals resulted in a collagen deposition running with the natural grain of the normal cornea versus the more circular swirling distribution in scarred control eyes.

EXAMPLE II

Radial keratotamies were performed on 4 primates (two treatments, two controls). The preoperative and surgical procedures were the same as those used in the cats of Example 1. At the end of the surgical procedure, the treatment group had a corneal mortar composition of the invention (CM) packed into the incisions. The CM was a mixture of 50 mg fibronectin, 2.6 g chondroitin sulfate, 1.3 ml of 1% collagen and 10 μg of epidermal growth factor, all to a total volume of 2.5 ml in saline solution. The control group received only the saline solution carrier.

Corneal flattening was measured at 7-day intervals, using a corneascope. The average flattening, in diopters, was determined for the treated eyes and the control eyes. FIG. 3 is a plot of diopters of flattening versus post-operative time. It can be seen from FIG. 3 that the treated eyes maintained a greater degree of corneal flattening throughout the post-operative period than the control eyes. After 77 days, the control eyes exhibited only an average of 0.1 diopters of flattening, whereas the treated eyes exhibited an average of 2.2 diopters of flattening.

What is claimed is:

1. A method for enhancing corneal healing following keratorefractive surgery in which incisions are made into the corneal stroma, the method comprising placing into the incisions a corneal mortar composition comprising at least one extracellular matrix material selected from the group consisting of fibronectin, collagen, vitronectin, elastin, laminin, actin, fibrinogen, chondroitin sulfate, heparin, keratin sulfate and hyaluronic acid and an ophthalmologically compatible carrier material, said composition having a sufficiently high viscosity to retain the extracellular matrix material within the incision under incision-healing conditions.

2. A method as claimed in claim 1, wherein the corneal mortar composition comprises an extracellular matrix material, a growth factor and an ophthalmologically compatible carrier material.

3. A method as claimed in claim 2, wherein the growth factor is epidermal growth factor.

4. A method as claimed in claim 1, wherein the extracellular matrix material is selected from fibronectin, chondroitin sulfate, and collagen.

5. A method as claimed in claim 1, wherein the corneal mortar composition comprises fibronectin and an ophthalmologically compatible carrier material.

6. A method as claimed in claim 1, wherein the corneal mortar composition contains from about 0.5% to about 90% by weight fibronectin.

7. A method as claimed in claim 1, wherein the corneal mortar composition comprises fibronectin, chondroitin sulfate and an ophthalmologically compatible carrier material.

8. A method as claimed in claim 1, wherein the corneal mortar composition comprises fibronectin, a growth factor and an ophthalmologically compatible carrier material.

9. A method as claimed in claim 1, wherein the corneal mortar composition comprises fibronectin, chondroitin sulfate, collagen and an ophthalmologically compatible carrier material.

10. A method as claimed in claim 1, wherein the corneal mortar composition comprises fibronectin, chondroitin sulfate, a growth factor and an ophthalmologically compatible carrier material.

11. A method as claimed in claim 5, wherein the corneal mortar composition comprises from about 2% to about 40% fibronectin and from about 98% to about 60% of an ophthalmologically compatible carrier material, based on total weight of the composition.

12. A method as claimed in claim 7, wherein the corneal mortar composition comprises from about 0.5% to about 40% fibronectin, from about 0.5% to about 75% chondroitin sulfate and from about 25% to about 99% of an ophthalmologically compatible carrier material, based on total weight of the composition.

13. A method as claimed in claim 8, wherein the corneal mortar composition comprises from about 2% to about 40% fibronectin, from about 60% to about 98% of an ophthalmologically compatible carrier material, based on total weight of the composition, and from about 0.01 μg/ml to about 100 μg/ml of a growth factor.

14. A method as claimed in claim 9, wherein the corneal mortar composition comprises from about 0.5% to about 40% fibronectin, from about 0.5% to about 75% chondroitin sulfate, from about 0.5% to about 50% collagen and from about 35% to about 98.5% of an ophthalmologically compatible carrier material.

15. A method as claimed in claim 10, wherein the corneal mortar composition comprises from about 0.5% to about 40% fibronectin, from about 0.5% to about 75% chondroitin sulfate, from about 25% to about 99% phosphate buffered saline solution, based on total weight of the composition, and from about 0.01 μg/ml to about 100 μg/ml of a growth factor.

* * * * *